United States Patent [19]

Schollmeyer et al.

[11] Patent Number: 5,036,854
[45] Date of Patent: Aug. 6, 1991

[54] LEAD INSERTION TOOL

[75] Inventors: Michael P. Schollmeyer, Anoka; Lawrence M. Kane, Roseville; James E. Revane, Minnitrista, all of Minn.

[73] Assignee: Angeion Corporation, Plymouth, Minn.

[21] Appl. No.: 480,450

[22] Filed: Feb. 15, 1990

[51] Int. Cl.⁵ .............................................. A61B 5/04
[52] U.S. Cl. .................................... 128/642; 128/785
[58] Field of Search ........... 128/642, 784, 785, 419 T; 606/132

[56] References Cited

U.S. PATENT DOCUMENTS

| | | | |
|---|---|---|---|
| 4,207,903 | 6/1980 | O'Neill | 128/785 |
| 4,244,375 | 1/1981 | Farrar et al. | 128/642 |
| 4,281,659 | 8/1981 | Farrar et al. | 128/642 |
| 4,672,979 | 6/1987 | Pohndorf | 128/784 |

Primary Examiner—Lee S. Cohen
Assistant Examiner—Krista M. Pfaffle
Attorney, Agent, or Firm—Schwartz & Weinrieb

[57] ABSTRACT

A lead insertion tool of a molded polymer including a main body and two movable fingers extending at an angle from one end of the main body for holding a cardiac sensing lead or cardiac pacing lead. The inner ends of the fingers are configured to grasp a pacing lead electrode body. A tubular member with finger tabs extends down and over the main body and down and over the extending fingers so that the ends of the fingers movingly engage about the pacing lead body when the tubular member is slid down the body of the lead insertion tool. The inner ends of the extending fingers can be geometrically configured to accept any particular pacing lead body member supporting the electrodes of the pacing lead.

4 Claims, 3 Drawing Sheets

LEAD INSERTION TOOL

CROSS REFERENCES TO CO-PENDING APPLICATIONS

This Application is related to U.S. Ser. No. 479,813, filed Feb. 15, 1990, entitled "Cardiac Sensing Lead", assigned to the same assignees.

BACKGROUND OF THE INVENTION

1. Field of the Invention

The present invention pertains to a pacing lead insertion tool, and more particularly, pertains to a lead insertion tool which is readily manufactured, readily sterilized and most importantly, readily used by a surgeon's single hand.

2. Description of the Prior Art

Prior art pacing lead insertion tools have been structurally complex in manufacture, not efficiently sterilized, and generally have required two handed operation which has been less than desirable.

The present invention overcomes the disadvantages of the prior art by providing a pacing lead insertion tool which is readily manufactured, easily sterilized and lends itself to one hand operation by a surgeon.

SUMMARY OF THE INVENTION

The general purpose of the present invention is a insertion tool for inserting electrodes in an electrode supporting body of a pacing lead or sensing lead into the heart in a screwing operation by a surgeon.

According to one embodiment of the present invention, there is provided a lead insertion tool including a body member of a suitable polymer and two springy moveable fingers extending from one end at an angle with respect to each other. The inner ends of the extending fingers are geometrically configured to grasp the body supporting a pacing electrode of a pacing lead. A slidable member engages around the body and the extending fingers, and includes finger tabs for support, as well as providing for grasping during a twisting rotation for screwing of the pacing electrode into the heart muscle. The outer member is slidable on the body member, providing for grasping of the lead body or disengagement of the extending fingers from the lead body when the outer member is slid upwardly over the main body so that the fingers disengage through the inherent memory of the plastic material away from the body of the pacing lead.

Significant aspects and features of the present invention include a lead insertion tool which is readily manufactured, such as through plastic injection molding techniques; is readily sterilized; and lends itself to one hand operation.

Another significant aspect and feature of the present invention includes the lead introducer particularly lends itself to epicardial pacing leads, especially for unipolar or bipolar leads.

Having thus described the embodiments of the present invention, it is a principal object hereof to provide an epicardial pacing and or sensing lead introducer for unipolar or bipolar pacing leads.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
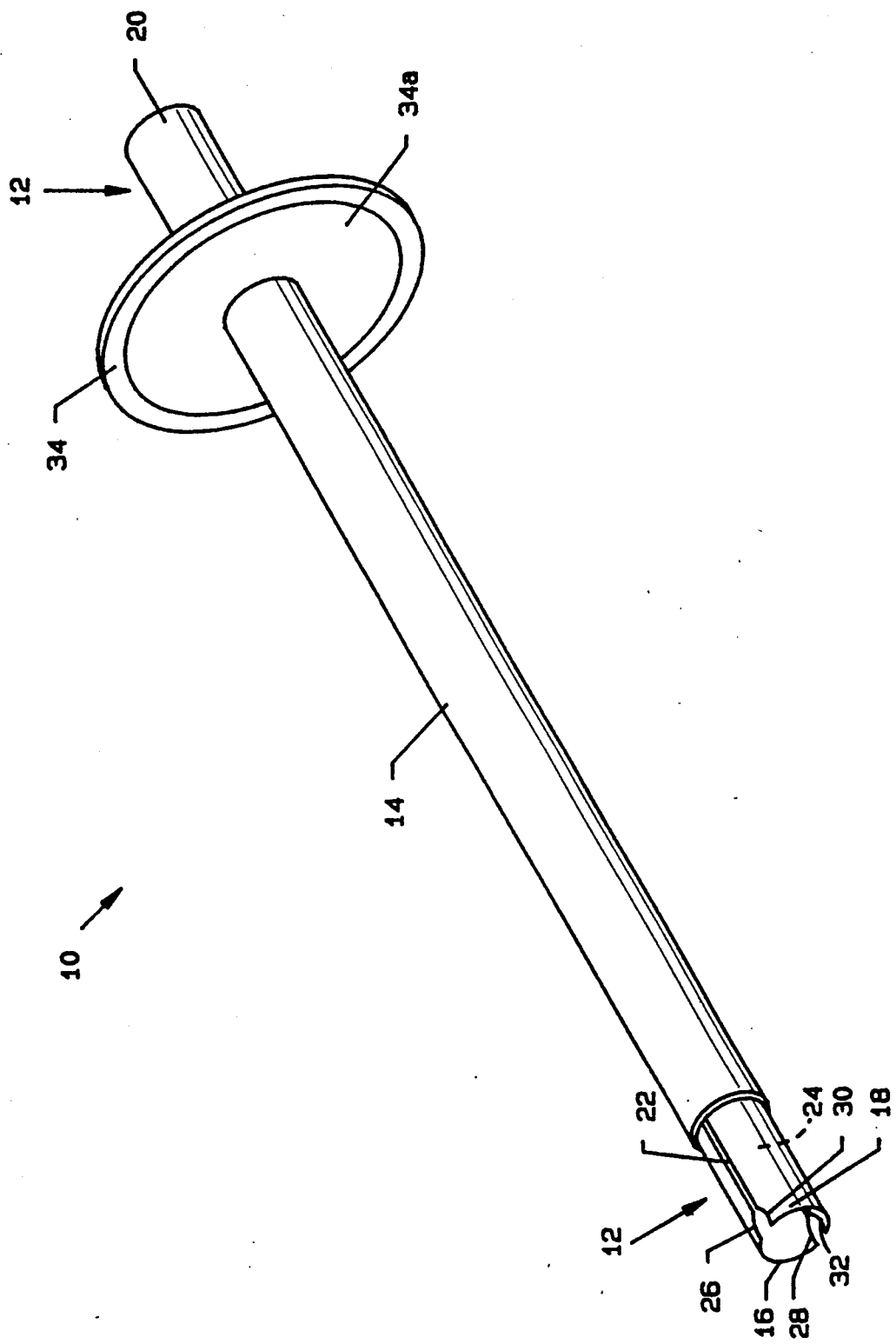
FIG. 1 illustrates a perspective view of a lead introducer.
Figure 2:
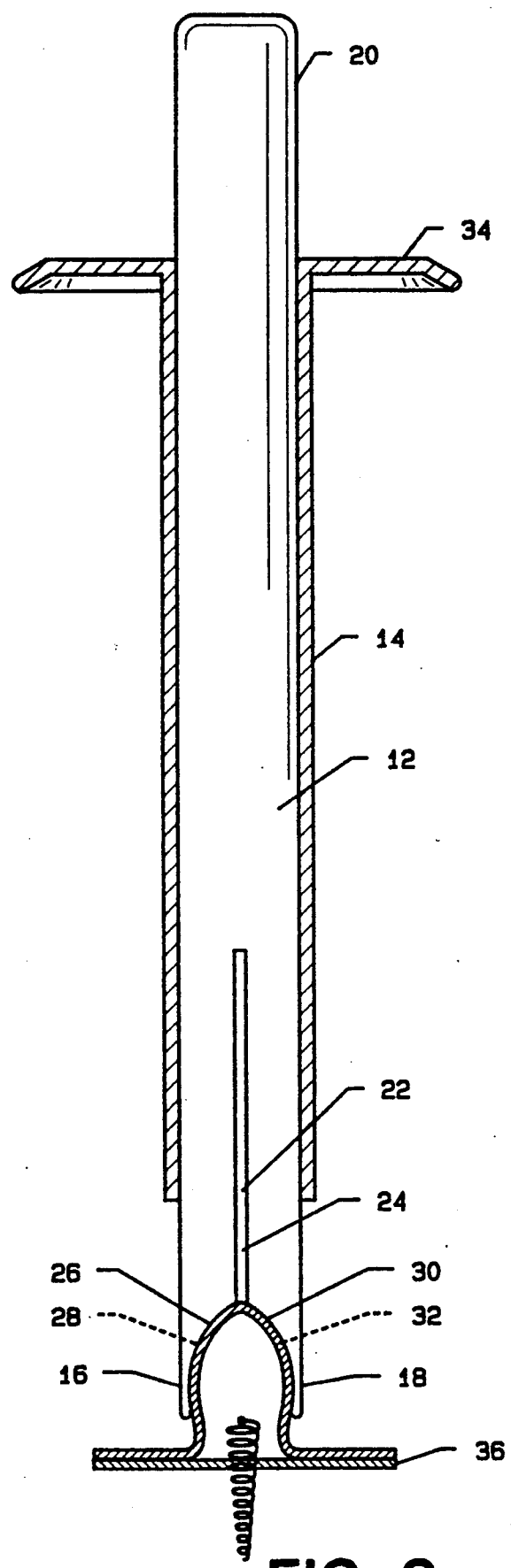
FIG. 2 illustrates the lead introducer engaged about a pacing or sensing lead; and, FIG. 3 illustrates the lead introducer prior to engagement with a pacing or sensing lead.
Figure 3:
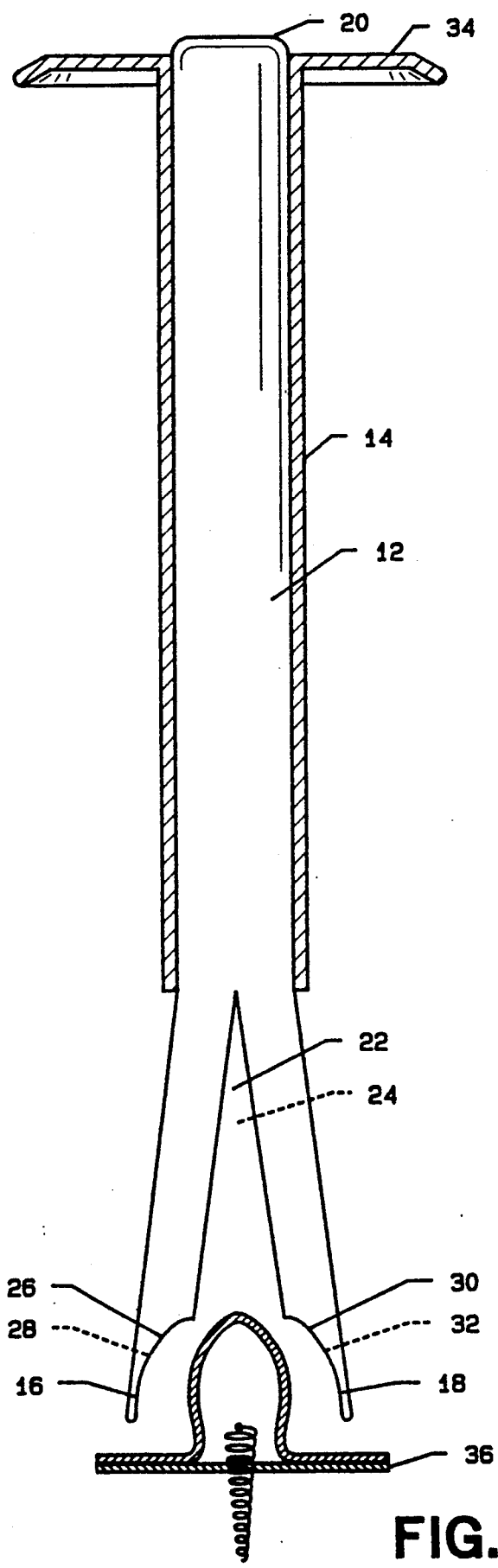

FIG. illustrates a perspective view of a lead introducer 10. The cylindrical shaped main body member 12 is partially contained and slides within a tubular member 14. The main body member 12 includes opposing moveable springy finger tabs 16 and 18 at one end and an opposing plain end 20. The finger tabs 16 and 18 are configured to accommodate and grasp a pacing or sensing lead body member as illustrated in FIGS. 2 and 3. The main body 12 also includes opposing slits 22 and 24 running a short distance on opposite sides of the main body 12 to help form the finger tabs 16 and 18. Finger tabs 16 and !8 include scalloped cutout pairs 26 and 28 and scalloped cutout pairs 30 and 32, respectively, which conform to the shape of a lead body member. The illustrated scalloped cutouts are for purposes of illustration only and are not to be construed as limiting in the scope of the invention. Of course, the scalloped cutouts can be in different shapes and forms to accommodate differently shaped pacing lead members. For example, the scalloped cutout pairs may be in a semi-ovoid shaped configuration which conforms to a semi-ovoid shaped lead member as shown in FIGS. 2 and 3 of the drawings. The finger tabs 16 and 18 are sprung outwardly from each other so that the finger tabs 16 and 18 diverge from each other at an angle when the tubular member 14 is advanced upwardly along the main body 12 so that a pacing lead is released from the finger tabs 16 and 18. The tubular member 14 includes handle 34, which is dished so that the surgeon can place two fingers against side 34a to assist in actuation of the main body 12 downwardly through the tubular member 14 by the surgeons thumb which activates the end 20 of the main body 12.

MODE OF OPERATION

FIG. 2 illustrates the lead introducer 10 engaged about a pacing lead 36 where all numerals correspond to those elements previously described. The surgeon uses this configuration to grip and to place the pacing lead 36. With reference to FIG. 3, the pacing lead is loaded by horizontal positioning of the pacing lead 36 substantially within the area of the finger tabs 16 and 18 and then sliding the tubular member 14 downwardly along the main body member 12 to force the outwardly sprung finger tabs 16 and 18 against the pacing lead 36 to grasp the pacing lead 36 as illustrated in FIG. 2.

FIG. 3 illustrates the lead introducer 10 prior to engagement with a passing lead where all numerals correspond to those elements previously described. This figure also illustrates the method of disengagement of a pacing lead 36 from the lead introducer 10 by actuation of the end 20 of the main body member 12 downwardly. As the tubular member 14 slides upwardly, the finger tabs 16 and 18 are removed from the confines of the tubular member 14 to allow the slits 22 and 24 to widen and also to allow the finger tabs 16 and 18 to spring apart from each other and releasing the pacing lead 36 from the scalloped cutouts 26–28 and 30–32.

Various modifications can be made to the present invention without departing from the apparent scope hereof.

I claim:

1. In combination, a lead insertion tool for holding, inserting, and removing a cardiac lead to be inserted within or removed from the heart of a patient, comprising:

an electrode system, defined within said cardiac lead, comprising an insulator disc, a conductive helical electrode projecting axially from a first surface of said insulator disc, and an electrode housing projecting axially from a second surface opposite said first surface of said insulator disc, said electrode housing, having a substantially semi-ovoid configuration in cross-section, being substantially coaxial with respect to said helical electrode;

a first tube having a proximal end and a distal end, wherein said distal end is partially severed in a longitudinal axial direction so as to define first and second distal end finger tabs, which are normally mutually biased away from each other, and wherein each of said first and second finger tabs have first and second oppositely disposed cut-out portions extending axially inwardly into said first tube from a leading surface portion of said distal end of said first tube wherein said cut-out portions have arcuate configurations corresponding to said semi-ovoid configuration of said electrode housing so as to envelopingly grasp said semi-ovoid electrode housing of said electrode system when said first and second finger tabs are biased toward each other while said leading surface portion of said distal end of said first tube can abuttingly engage said insulator disc of said electrode system; and a second tube having a proximal end and a distal end, and having a diameter permitting said second tube to slidably move over said first tube between a retracted position at which said first and second finger tabs are permitted to diverge away from each other so as to release said electrode housing, and an extended position at which said mutual bias of said first and second finger tabs is overcome so as to thereby cause said first and second finger tabs, and said first and second cut-out portions, to be biased toward each other so as to firmly grasp said electrode housing.

2. The combination as set forth in claim 1, further comprising:

handle means connected to said second tube for assisting an operator to slidably move said second tube with respect to said first tube.

3. The combination as set forth in claim 2, wherein said handle means comprises:

an annular disc integrally attached to said second tube at said proximal end thereof.

4. The combination as set forth in claim 1, wherein:

said first tube has a predetermined length such that said proximal end thereof projects axially beyond said proximal end of said second tube when said second tube is disposed at said extended position so as to permit an operator to operate said tool by means of a one-handed operational mode when it is desired to release said tool from said cardiac lead.

* * * * *